US00PP26288P3

(12) United States Plant Patent
Wright et al.

(10) Patent No.: US PP26,288 P3
(45) Date of Patent: Jan. 5, 2016

(54) BLUEBERRY PLANT NAMED 'C04-051'

(50) Latin Name: ***Vaccinium corymbosum* hybrid**
Varietal Denomination: C04-051

(71) Applicants: CostaExchange Pty Ltd., Corindi (AU); Florida Foundation Seed Producers, Inc., Marianna, FL (US)

(72) Inventors: Gary Wright, Corindi Beach (AU); Paul Lyrene, Micanopy, FL (US)

(73) Assignees: COSTAEXCHANGE PTY LTD., Corindi (AU); FLORIDA FOUNDATION SEED PRODUCERS, INC., Marianna, FL (US)

( * ) Notice: Subject to any disclaimer, the term of this patent is extended or adjusted under 35 U.S.C. 154(b) by 119 days.

(21) Appl. No.: 13/999,627

(22) Filed: Mar. 13, 2014

(65) Prior Publication Data

US 2014/0283235 P1 Sep. 18, 2014

Related U.S. Application Data

(60) Provisional application No. 61/851,798, filed on Mar. 13, 2013.

(51) Int. Cl.
*A01H 5/00* (2006.01)
*A01H 5/08* (2006.01)

(52) U.S. Cl.
USPC ..... Plt./157
CPC ..... *A01H 5/08* (2013.01)

(58) Field of Classification Search
USPC ..... Plt./157
See application file for complete search history.

*Primary Examiner* — Annette Para
(74) *Attorney, Agent, or Firm* — Hahn Loeser & Parks LLP

(57) ABSTRACT

A new and distinct cultivar of blueberry (*Vaccinium corymbosum* hybrid) plant named 'C04-051', characterized by its Upright to semi-upright plant growth habit and strong plant growth vigor, low chilling requirement, large fruit size, good fruit flavor, firm fruit suited to handling and low scarring on the fruit. This combination results in higher quality fruit with a later availability than other varieties.

4 Drawing Sheets

Latin name of the family, genus, and species:
Family—Ericaceae.
Genus—*Vaccinium.*
Species—*corymbosum* hybrid.
Variety denomination: The new blueberry plant claimed is of the variety denominated 'C04-051'.

BACKGROUND OF THE INVENTION

The present invention relates to a new and distinct perennial variety of *Vaccinium corymbosum* hybrid (blueberry), which has been given the variety denomination of 'C04-051'. The new variety 'C04-051' shows distinctive traits such as strong growth vigor, good acidity and sweetness balance in the fruit, low scarring strong fruit firmness, low chilling requirement. The new variety 'C04-051' is intended for use as fresh fruit for shipping, customer pick and processing markets and as a home garden plant.

The new blueberry cultivar is a selection resulting from seedlings produced in a controlled breeding programme of *Vaccinium* varieties in Florida, USA in 2002 from a cross of the blueberry variety known as 'FL02-043' (seed parent) (unpatented) and the blueberry variety known as 'FL89-119' (pollen parent) (unpatented). The seed from the cross was sown and grown in Corindi Beach, New South Wales, Australia. The new cultivar was discovered and selected in 2004 as a single plant within a population of seedlings resulted from the controlled cross, in an experimental block in the field at Corindi Beach, New South Wales, Australia, and has since been named 'C04-051'. Selection criteria were a combination of strong growth vigor, low chilling requirement, good fruit flavor and low scarring on the fruit. The new variety was subsequently evaluated for a number of years at the commercial farm at Corindi Beach, New South Wales, Australia.

Asexual reproduction of the new variety 'C04-051' by softwood cutting propagation since 2004 at Corindi Beach, New South Wales, Australia has demonstrated that the new variety reproduces true to type with all of the characteristics, as herein described, firmly fixed and retained through successive generations of such asexual propagation, with the clones phenotypically identical to the original plant.

The seed parent 'FL02-043' is characterized by an upright growth habit and late timing ripening of fruit. The pollen parent 'FL89-119' is characterized by medium plant growth vigor, early timing of ripening of fruit and semi-upright growth habit. The new variety 'C04-051' differs from the female parent 'FL02-043' and the male parent 'FL89-119' in that 'C04-051' has a mid-season cropping timing. The new variety 'C04-051' has a plant growth habit that is intermediate between the female parent's upright and the male parent's semi-upright growth habit. The new variety 'C04-051' also differs from the male parent in that 'C04-051' has stronger plant vigor.

SUMMARY OF THE INVENTION

The following characteristics of the new variety have been repeatedly observed and can be used to distinguish 'C04-051' as a new and distinct variety of *Vaccinium corymbosum* hybrid:

1. Low chilling requirement
2. Strong growth vigor
3. Upright to semi-upright plant growth habit
4. Large fruit size 5. Good fruit flavor
6. Low scarring on the fruit The new variety 'C04-051' differs from the female parent 'FL02-043' and the male parent 'FL89-119' in that 'C04-051' has a mid-season cropping timing. The new variety 'C04-051' has a plant growth habit that is intermediate between the female parent's upright and the male parent's semi-upright growth habit. The new variety 'C04-051' also differs from the male parent in that 'C04-051' has stronger plant vigor. The new blueberry variety 'C04-051' has maintained its distinguished characteristics throughout successive asexual propagation.

BRIEF DESCRIPTION OF THE DRAWINGS

The accompanying photographic illustration shows typical specimens in full color of the foliage and fruit of the new variety 'C04-051'. The colors are as nearly true as is reasonably possible in a color representation of this type.

Figure 1:
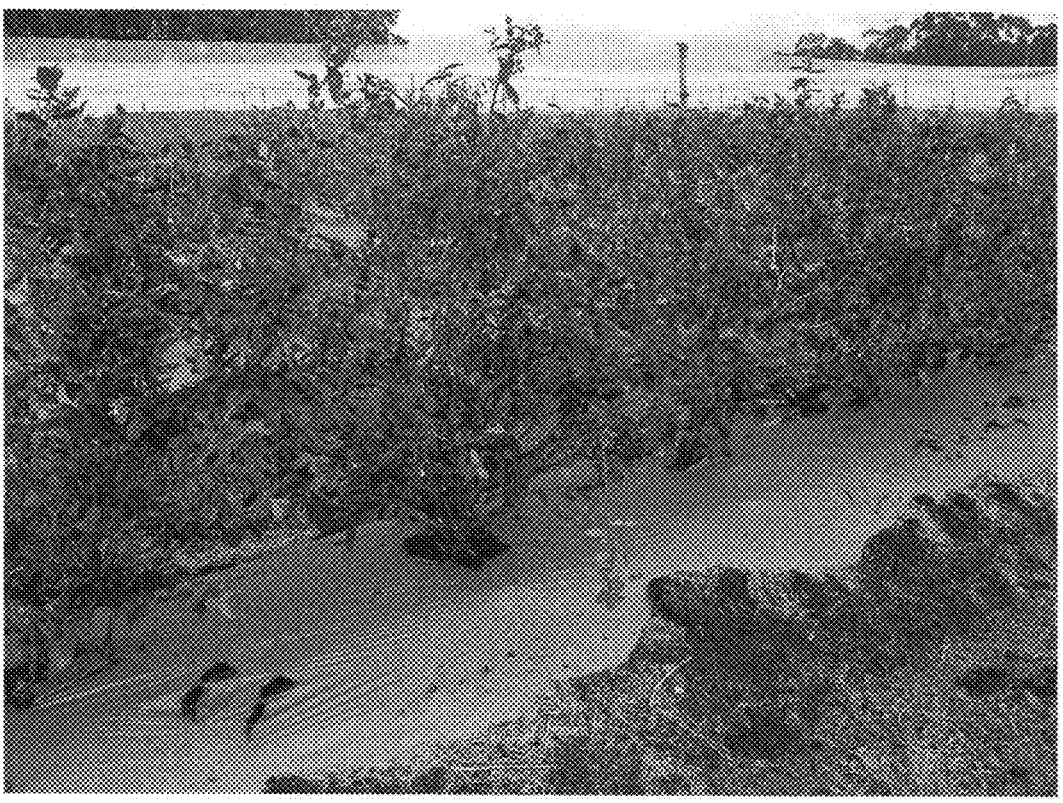
FIG. 1 is a photograph of the new variety 'C04-051' demonstrating the plant's upright to semi-upright growth habit.
Figure 2:
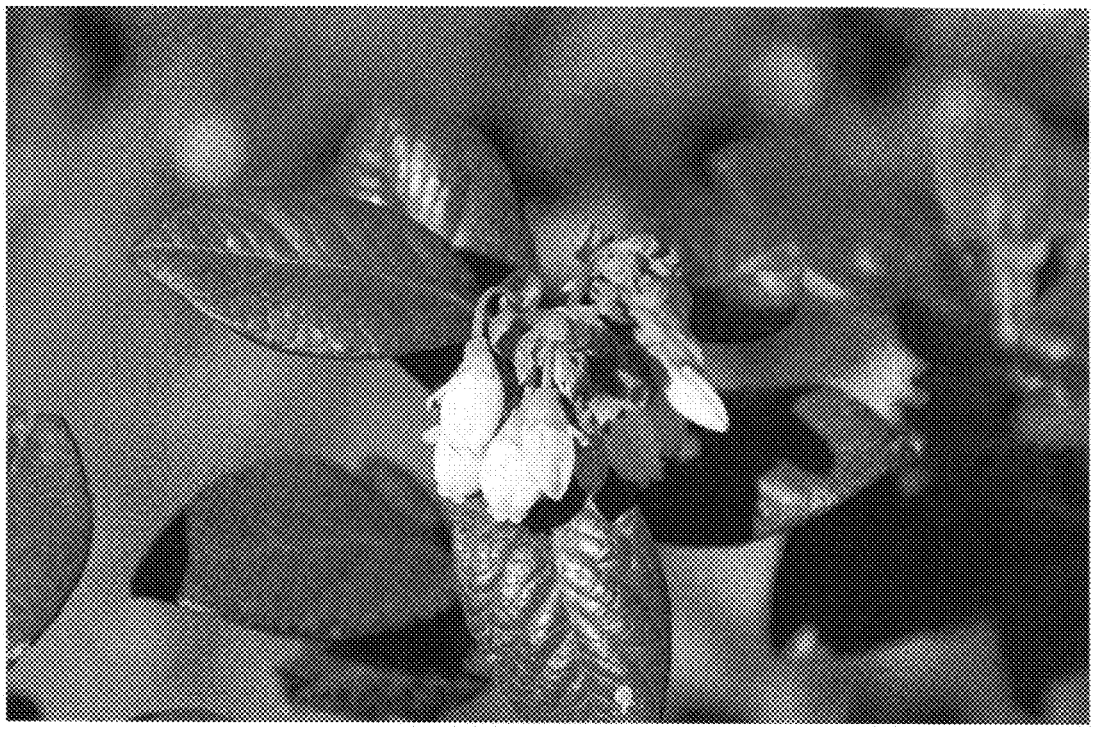
FIG. 2 is a photograph of the flowers of the new variety 'C04-051'.
Figure 3:
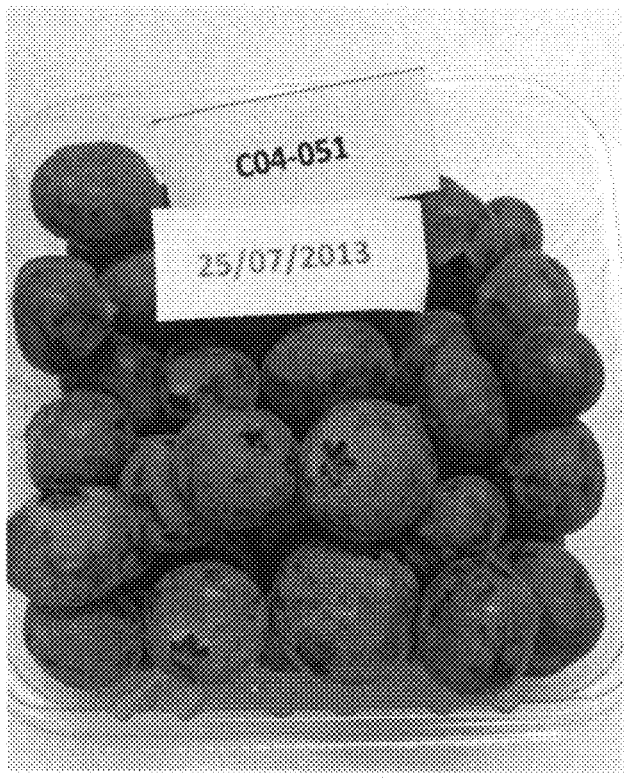
FIG. 3 is a photograph of the fruit of the new variety 'C04-051'.
Figure 4:
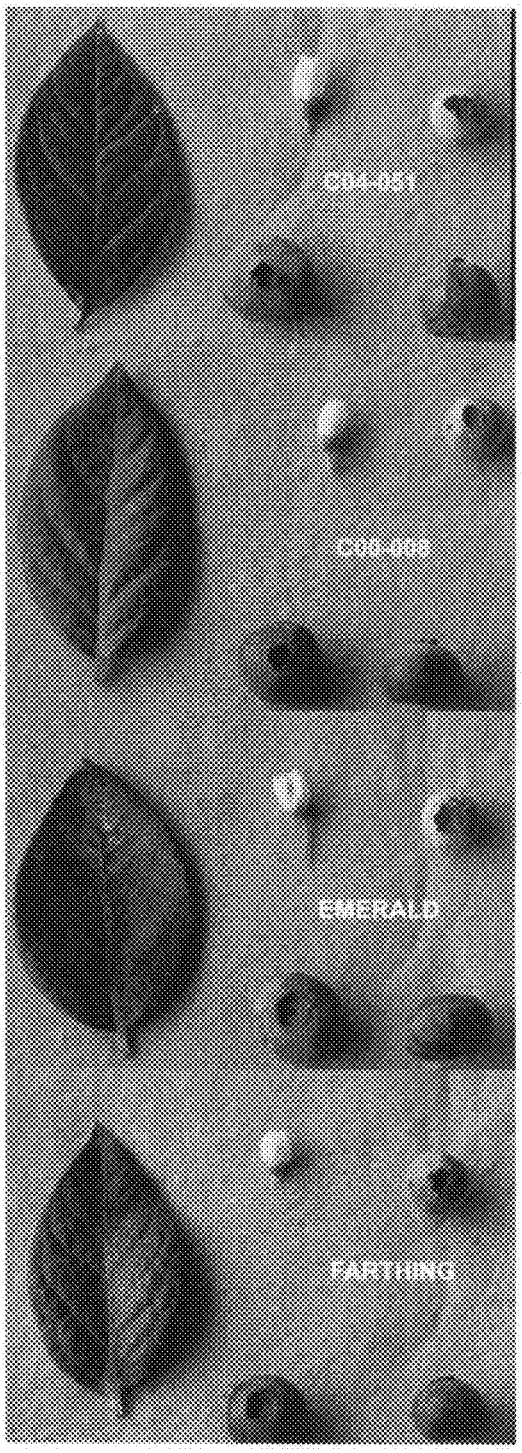
FIG. 4 is a photograph of the new variety 'C04-051', showing parts of the plant in comparison with 3 other varieties.

The colors in the photographs are as close as possible with the photographic and printing technology utilized. The color values cited in the detailed botanical description accurately describe the colors of the new blueberry.

DETAILED BOTANICAL DESCRIPTION

The following detailed description sets forth the distinctive characteristics of 'C04-051'. The data which defines these characteristics was collected from asexual reproductions of the original selection. Dimensions, sizes, colors, and other characteristics are approximations and averages set forth as accurately as possible. The plant history was taken on plants approximately 4 years of age, and the descriptions relate to plants grown in the field in Corindi Beach, New South Wales, Australia. Descriptions of fruit characteristics were made on fruit grown in Corindi Beach, New South Wales, Australia. Color designations are from R.H.S. Chart—edition 2007.

Classification:

*Family.*—Ericaceae.
*Genus.*—*Vaccinium.*
*Species.*—*corymbosum* hybrid.
*Common name.*—blueberry.

Parentage:

*Seed parent.*—'FL02-043' (unpatented).
*Pollen parent.*—'FL89-119' (unpatented).

Market class: Suitable for the Commercial, Hand Harvest Fresh, Processed, and Home Garden Markets.

PLANT

*Parentage.*—'FL02-043'×'FL89-119'.
*Growth habit.*—Upright to semi-upright.
*Growth.*—Vigorous.
*Chilling requirement*—Low chill.
*Leafing.*—Moderate during the winter and medium to high during the summer under the environment at Corindi Beach, NSW, Australia.

FOLIAGE

*Time of beginning of leaf bud burst.*—Around middle August.
*Leaf color* (*top side*).—Near to green group 137 A and the vein color near to green group N144 A.
*Leaf shape.*—Elliptic.
*Leaf margins.*—Entire.
*Leaf length.*—Average 65 mm (range 58-75 mm).
*Leaf width.*—Average 35 mm (29-42 mm).
*Leaf nectarines.*—Absent.

Petioles:

*a. Length.*—Average 3.8 mm (range 2.4-5 mm).

FLOWERS

*Time of beginning of flowering.*—Medium around middle August.
*Time of* 50% *anthesis.*—Average 15$^{th}$ August.

Corolla:

*a. Length.*—Average 6.4 mm (range 5.2-8.1 mm).
*b. Anthocyanin coloration of corolla.*—Absent.

FRUIT

*Time of fruit ripening.*—Medium.
*Unripe fruit color.*—Near to yellow-green group 145B.
*Ripe berry color.*—Near to Blue group 103A.
*Berry surface wax abundance.*—Strong to very strong.
*Berry weight.*—Average 2.8 g.
*Berry diameter.*—Average 17 mm (range 16.3-18.3 mm).
*Fruit stem scar.*—Dry, average 2 mm (range 1.6-2.5 mm).
*Sweetness when ripe.*—Medium (average 14 Brix).
*Uses.*—Fresh fruit.

SEED

*Seed abundance in fruit.*—Ranging between 3-11 viable seeds.
*Seed length.*—Average 2.1 mm (range 1.8-2.3 mm).

The invention claimed is:

1. A new and distinct variety of blueberry plant named 'C04-051', substantially as illustrated and described herein.

* * * * *